United States Patent [19]
Nowakowski

[11] Patent Number: 5,327,887
[45] Date of Patent: Jul. 12, 1994

[54] CARDIOPULMONARY RESUSCITATION DEVICE

[76] Inventor: Ludwik Nowakowski, 735, Downing Street, Kingston, Ont., Canada, K7M 5N1

[21] Appl. No.: 8,317

[22] Filed: Jan. 25, 1993

[51] Int. Cl.⁵ .................................... A61H 31/00
[52] U.S. Cl. .................. 128/204.21; 128/204.18; 128/202.13; 128/205.13; 601/41
[58] Field of Search .............. 128/200.24, 28, 53, 128/54, 204.18, 204.21, 202.13, 204.28, 205.14, 205.13

[56] References Cited

U.S. PATENT DOCUMENTS

| | | | |
|---|---|---|---|
| 3,425,409 | 2/1969 | Isaacson | 128/28 |
| 3,905,363 | 9/1975 | Dudley | 128/204.24 |
| 4,198,963 | 4/1980 | Barkalow | 128/53 |
| 4,273,114 | 6/1981 | Barkalow | 128/53 |
| 4,297,999 | 11/1981 | Kitrell | 128/205.16 |
| 4,326,507 | 4/1982 | Barkalow | 128/54 |
| 4,338,924 | 7/1982 | Bloom | 128/28 |
| 4,361,140 | 11/1982 | Barkalow | 128/28 |
| 4,397,306 | 8/1983 | Weisfeldt | 128/28 |
| 4,424,806 | 1/1984 | Newman | 128/28 |
| 4,702,231 | 10/1987 | Arpin | 128/28 |
| 5,211,170 | 5/1993 | Press | 128/204.18 |

FOREIGN PATENT DOCUMENTS

| | | |
|---|---|---|
| 739228 | 7/1966 | Canada . |
| 766539 | 9/1967 | Canada . |
| 775366 | 1/1968 | Canada . |
| 979767 | 12/1975 | Canada . |
| 1231873 | 1/1988 | Canada . |

*Primary Examiner*—Edgar S. Burr
*Assistant Examiner*—Eric P. Raciti

[57] ABSTRACT

A portable self-contained apparatus for delivery of cardiopulmonary resuscitation (CPR) including an arrangement for applying cyclical chest compression and a lung ventilator operatively connected to the chest compression arrangement to deliver volume control ventilation simultaneously with chest compression or asynchronously with chest compression after a predetermined number of compressions. Span adjustment for the thumper accommodates patients with different chest sizes and also adjusts the length of stroke and force of the chest compression thumper as well as the volume of the ventilator output. A ratchet connected to the thumper allows natural expansion of the chest during inhalation by the patient while allowing compression by the apparatus. A control arrangement allows selectively operating the chest compression thumper and the ventilator in a predetermined sequence as well as monitor a patient's vital signs.

10 Claims, 9 Drawing Sheets

CARDIOPULMONARY RESUSCITATION DEVICE

FIELD OF THE INVENTION

This invention relates to a new cardiopulmonary resuscitation (CPR) device that is portable, simple to install on a patient, and provides effective CPR on a wide range of patient sizes. The device provides a means of adjusting several CPR parameters with the adjustment of a single parameter relating to patient chest size.

The device is capable of delivery of ventilation during compression (VDC), asynchronous ventilation (AV) between preselected number of chest compressions and ventilation without compression (VWC) when required.

BACKGROUND OF THE INVENTION

It is well known that victims of a heart attack should receive immediate aid in the form of cardiopulmonary resuscitation following an attack. The time delay from the moment of an attack to the initiation of CPR by a rescuer and the effectiveness of the CPR greatly influences the chance of survival of the victim. In an emergency, in addition to minimizing the delay for initiating treatment, it is equally important that the CPR received is highly effective, requiring the minimum of operator input to ensure effectiveness. Research has demonstrated that the effectiveness of the CPR is improved when chest compression is performed simultaneously with lung ventilation in addition to asynchronous lung ventilation cycles between a selected number of compression cycles. It has also been shown that increased thorax pressure, and not the heart pumping action during chest compression, causes valves in the jugular veins to open and pass blood through. These valves close during decompression. While there are devices available that can deliver chest compression that are coupled with ventilation, these systems are highly complex requiring a high level of operator skill to optimize performance parameters. Serious injury to the patient can be the result of improperly set parameters including fracture of the sternum or lung rupture if too much pressure is applied.

As well, victims of heart attacks are not limited to a particular body size or weight. The victim of a heart attack can range in weight and size from that of a small child to that of a large and possibly overweight adult. The CPR required by different sized victims therefore varies. For example, smaller victims, with a smaller chest require a lower compression force, lower compression displacement and lower ventilation volumes and pressures. Similarly, those victims with a larger chest size require a higher compression force, a higher compression displacement and higher ventilation volumes and pressures.

U.S. Pat. No. 4,397,306 discloses an integrated, non-portable, system for cardiopulmonary resuscitation and circulation support. This device comprises a chest compression means in conjunction with a lung ventilation means capable of providing high pressure ventilation synchronously with chest compression, a low pressure ventilation means for inflating the lungs at low pressure between a selected number of compression cycles and a negative pressure ventilator for deflating the lungs between chest compressions. The device is further comprised of a valve means for operating one of the ventilators, a means for restricting the abdomen to exert pressure thereon and a control means for selectively operating the chest compression means, the ventilating means, the valve means and abdomen restricting means in a selected sequence and for selected durations.

The control of this device is highly complex, requiring a high degree of operator skill to control in order to ensure optimization of input and output parameters and, hence, patient parameters that indicate recovery. Furthermore, this device does not describe a means of effectively adjusting parameters of the device to provide effective and safe CPR to patients of different sizes.

U.S. Pat. No. 4,424,806 discloses an automated ventilation, cardiopulmonary resuscitation and circulatory assistance apparatus. This device includes an airway apparatus, a vest including an inflatable bladder for compressing chest and abdominal restrainer including an inflatable bladder. An airway, vest and abdominal pneumatic control apparatus to alternately inflate and deflate the patient lungs, the vest bladder and the abdominal restrain bladder, respectively. The device has a provision for selectively adjusting the volume of gas that is coupled to the patient's lungs, and the maximum pressure that are obtained in the vest bladder and the abdominal restraint bladder. An electronic control means which allow selection of operation mode and control lung vest bladder and abdominal restrain bladder inflation and deflation by controlling respective time signals.

The control of the device is complex and requires from the operator good knowledge of human physiology to properly adjust the pressure-volume control ventilation means for delivery of simultaneously ventilation with chest compression and inflation of bladders for chest compression and abdominal restrain. Incorrect adjustment of any of these parameters, malfunction of the control system or component failure such as chest compressor control valve or pressure regulator occurs, high ventilation pressure would enter a patient lungs. In an absence of counteracting intrathoracic pressure, which is generated during chest compression may lead to the lungs rupture.

U.S. Pat. No. 4,326,507 discloses cardiopulmonary resuscitation device that cyclically compresses a patient's chest and simultaneously ventilates the patient's lungs to a safe limiting pressure over a period of time. This creates a pressure increase in the patient's thorax during systole that enhances blood perfusion. In addition continuous application of ventilation pressure during the diastolic portion of the compression cycle enhances blood gas exchange.

The simultaneous application of a benign limiting pressure during chest compression though enhances patient's safety but lowers the intrathorax pressure and in consequence takes away the benefits of high pressure ventilation during chest compression thus decrease the efficiency of CPR procedure.

Canadian Patent 979,767 discloses a self-contained resuscitation device that can provide cardiac massage with artificial respiration to a patient. The device provides a manually adjustable chest compression means and asynchronous ventilating means. The device does not disclose a means for adjusting ventilation and ventilation during compression volumes, thumping stroke and thumping force simultaneously with adjusting the span adjustment (distance between the thumper and base to accommodate a patient's chest).

Other related patents include Canadian Patent 739,228 disclosing a heart massage apparatus with compressed gas actuating means, Canadian Patent 766,539 disclosing an external heart massage apparatus, Canadian apparatus 775,366 disclosing an external cardiac massage apparatus, U.S. Pat. No. 3,425,409 disclosing an external cardiac massage apparatus with asynchronous ventilation, U.S. Pat. No. 4,297,999 disclosing a portable resuscitation apparatus to be used in conjunction with manual external cardiac massage, U.S. Pat. No. 4,338,924 disclosing a CPR device that provides ventilation from conventional compressed gas cylinders, U.S. Pat. No. 4,702,231 discloses a portable heart massage apparatus driven by electrical motor. The motor is used to actuate a pair of hydraulic cylinders connected together in a "slave" arrangement. The "slave" cylinder is mounted on a platform adopted to be strapped to the chest of the victim, with the slave cylinder having a ram that pushes rhythmically against the sternum to squeeze the heart.

With pneumatic, volume driven chest compressor the compression depth is effected by a patient chest rigidity, thus may require subsequent corrections to the depth of chest compression means. This can be done only by interruption of chest compression because the adjustment mechanism is mounted on rotating speed reduction gear shaft. This apparatus does not have a ventilator but merely a provision to drive mechanical ventilator, neither describes the ability to deliver ventilation simultaneously with chest compression nor the adjustment of critical CPR parameters. Canadian Patent 1,231,873 discloses an external cardiac massage device.

OBJECTS OF THE INVENTION

It is, therefore, an object of the invention to provide a CPR device that is safe, effective, portable, and self contained. This device allows an operator to alternate between three different modes of operation:

1. Volume control "Asynchronous Ventilation" (AV) where ventilation is delivered to a patient's lungs after preselected number of chest compressions.
2. Volume control "Ventilation During Compression" (VDC) where ventilation is delivered to patient's lungs simultaneously with chest compression.
3. Volume control "Ventilation Without Compression" (VWC) where ventilation is delivered to patient's lungs without chest compression.

Another objective of the invention is to provide a device that eliminates a need for adjustment of critical CPR parameters by operator. Adjustments of such parameters as: thumping length of stroke and force, asynchronous ventilation (AV) volume, ventilation during compression (VDC) volume and ventilation without compression (VWC) volume are slaved to the adjustment of single parameter, namely span adjustment. Span adjustment is define as the distance between the (thumper) which compresses patient's chest and the base member that supports patient's back. The span adjustment is carry out by operator during device initial set up on a patient. The span adjustment and the CPR critical parameters adjustments are proportional to the patient's chest size.

BRIEF STATEMENT OF THE INVENTION

In accordance with one embodiment of the present invention, there is provided a device for use in cardiopulmonary resuscitation comprising:
a base member;
chest compression means adjustably mounted on said base member and adapted to be positioned over a patient's sternum and operable to compress said sternum at selected intervals with a selected force;
means to drive said chest compression means;
means operatively coupled with said driving means to provide low pressure, volume control ventilation asynchronously with chest compression;
ventilation-during-compression means operatively coupled with said driving means to provide ventilation synchronously with chest compression; and
means to count a selected number of chest compression cycles and then disengage said chest compression means from said driving means so as to enable a low pressure ventilation cycle, and to re-engage with said driving means following said low pressure ventilation cycle.

A preferred embodiment of the invention further includes an adjustment means adapted to provide thumping length of stroke force adjustment, ventilation volume adjustment, and ventilation-during-compression volume adjustment simultaneously and proportionally to span adjustment.

DETAILED DESCRIPTION OF THE PREFERRED EMBODIMENT

Figure 1:
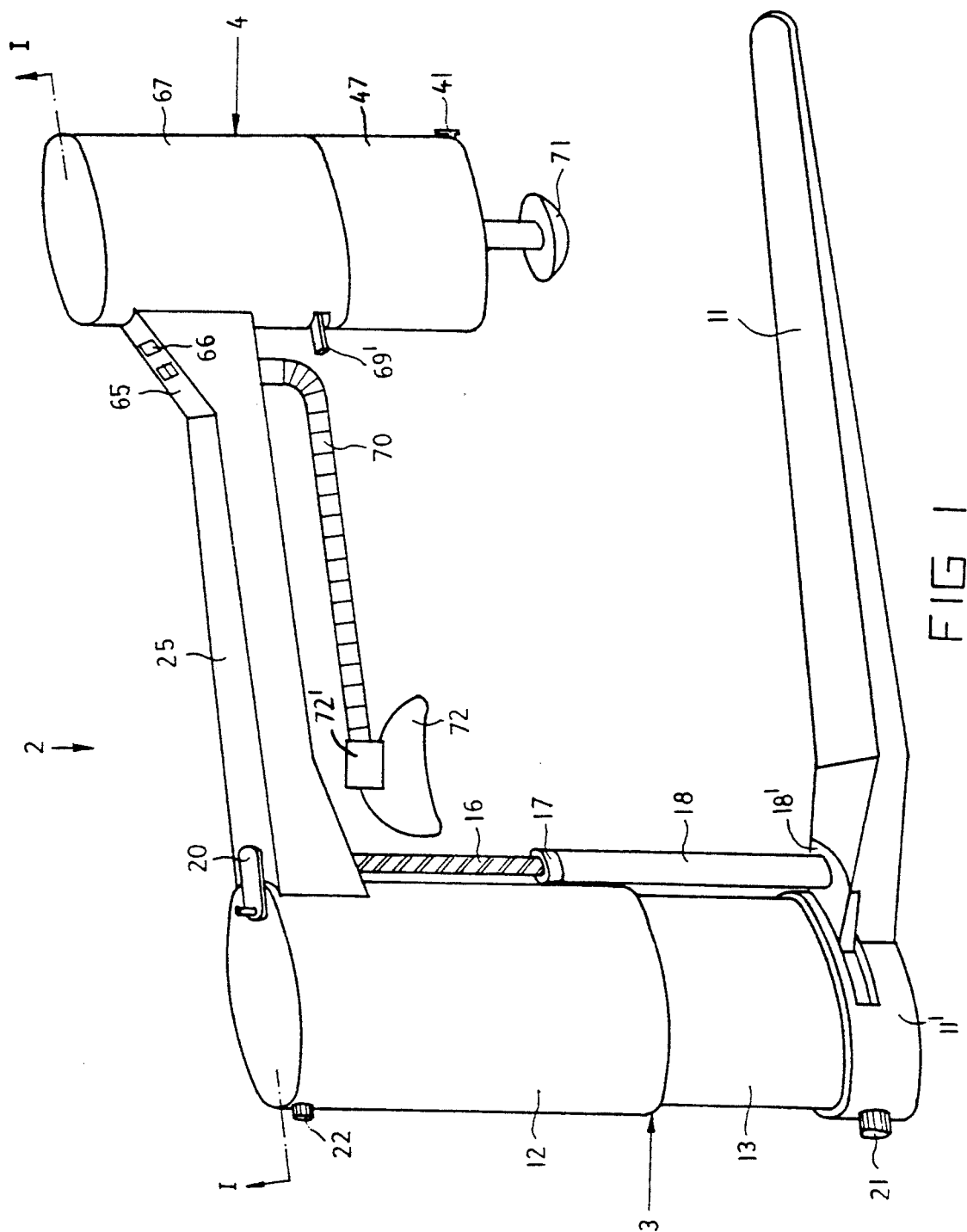
FIG. 1 is a perspective view of a preferred embodiment of the invention.
Figure 2:
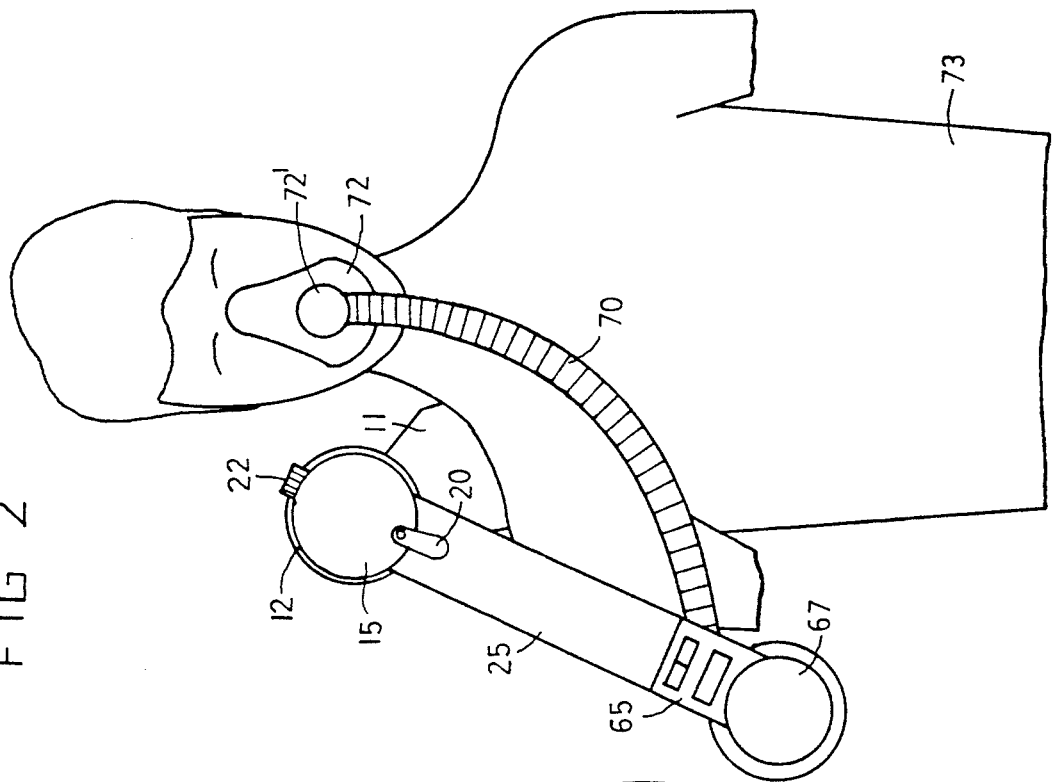
FIG. 2 is a plan view of the embodiment shown in FIG. 1 in position for simultaneous chest compression and ventilation of a patient.
Figure 3:
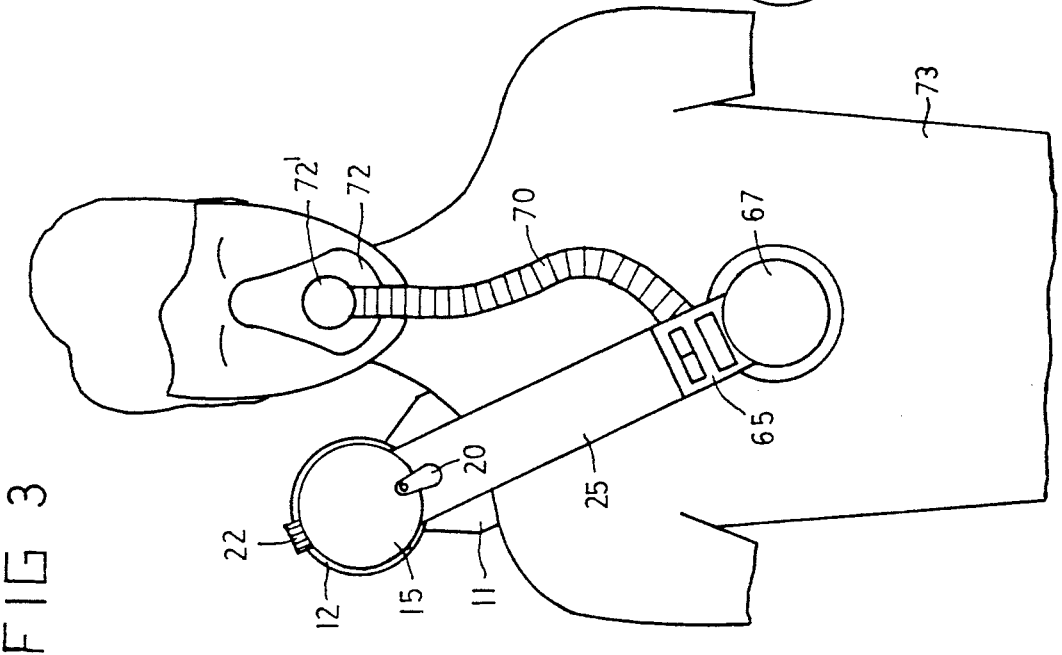
FIG. 3 is a plan view of the embodiment shown in FIG. 1 in position for ventilation of a patient.

With reference to the drawings, and specifically to FIGS. 1-3, the CPR device 2 is comprised of the following main components. The CPR device 2 has a base 11 which is designed to slide under the back of a patient 73 and provide vertical stability to the CPR device 2. The base 11 is pivotally connected to a vertical upright 3 and a generally horizontal arm 25. Movement of vertical upright 3 relative to the base 11 is inhibited by spring detent arm locking mechanism 21. Sufficient lateral force applied to the arm 25 will disengage the arm locking mechanism 21 and allow movement of the vertical upright 3 and arm 25 relative to the base 11. The vertical upright 3 is comprised of two upright telescoping columns, the upper external upright telescope column 12 and the lower internal upright telescope column 13 mounted on the cylindrical base end 11'. The external upright telescope column 12 and the internal upright telescope column can both be moved longitudinally and axially with respect to one another. The vertical upright 3 also comprises an upright telescope column partition 13' providing a cover to battery 45 and separating it from resilient reservoir 23. A battery compartment cover 14 is also provided within cylindrical base end 11'. The top of vertical upright 3 has a reservoir compartment lid 15 to facilitate access to the interior of said upright 3.

The arm 25 which is mounted on column 12 at one end thereof includes a valve 46 which supports the proximal end of a ventilation tube 70 which has a ventilation mask 72 and ventilation valve 72' at the distal end thereof. The arm 25 is also connected to a housing 4 which supports the components for driving the chest compression means of thumper 71. The housing 4 is comprised of drive mechanism housing 67 and VDC cylinder 47. The relative positions of the main structural components can be adjusted so as to provide the necessary clearance in order that a patient 74 can be positioned between the thumper 71 and base 11 as indicated in FIGS. 2 and 3.

Figure 4:
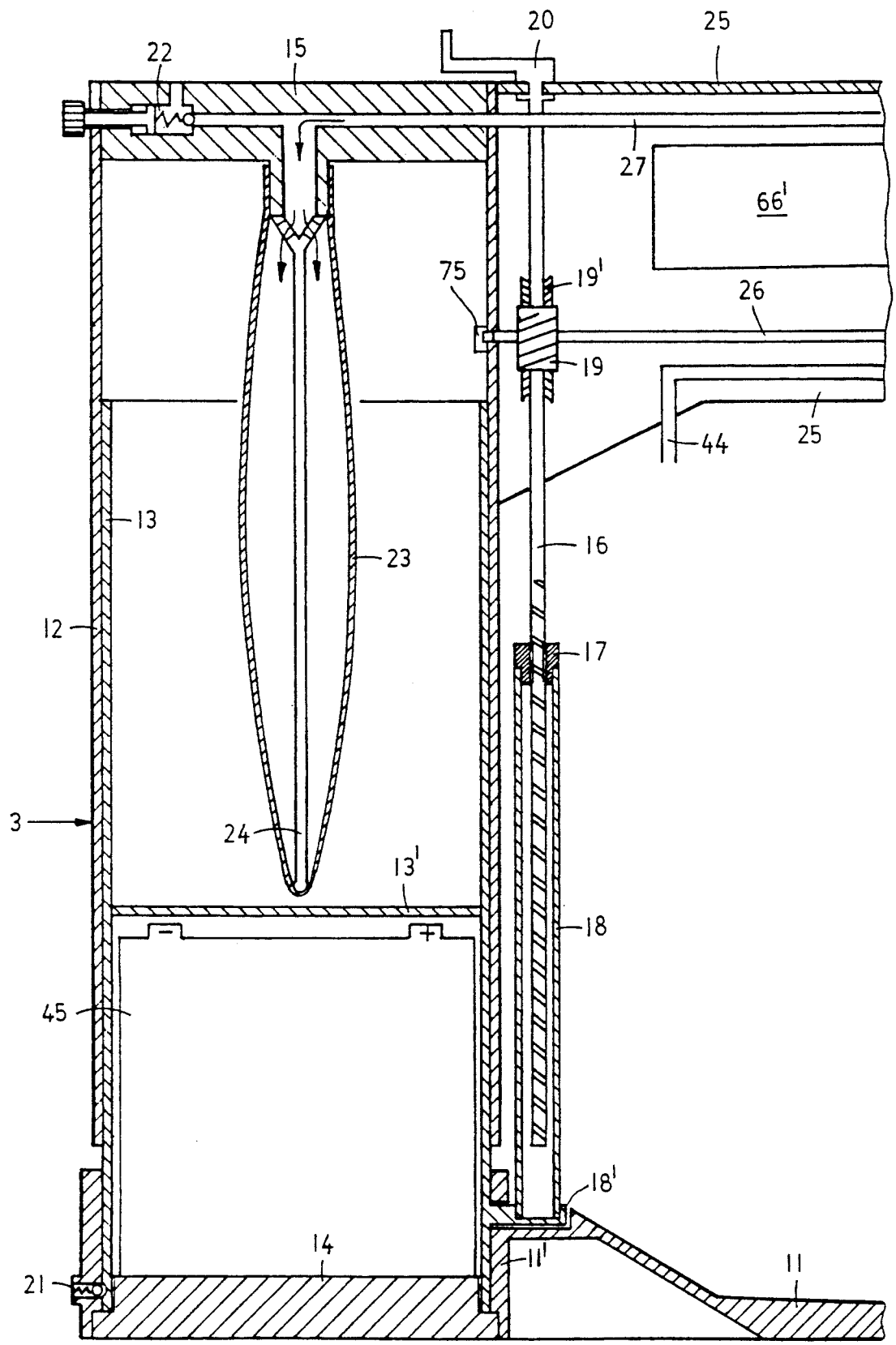
FIG. 4 is a cross-sectional view of the vertical upright of the embodiment shown in FIG. 1 showing details of the span adjustment crank and the resilient reservoir during filling at line I—I.
Figure 5:
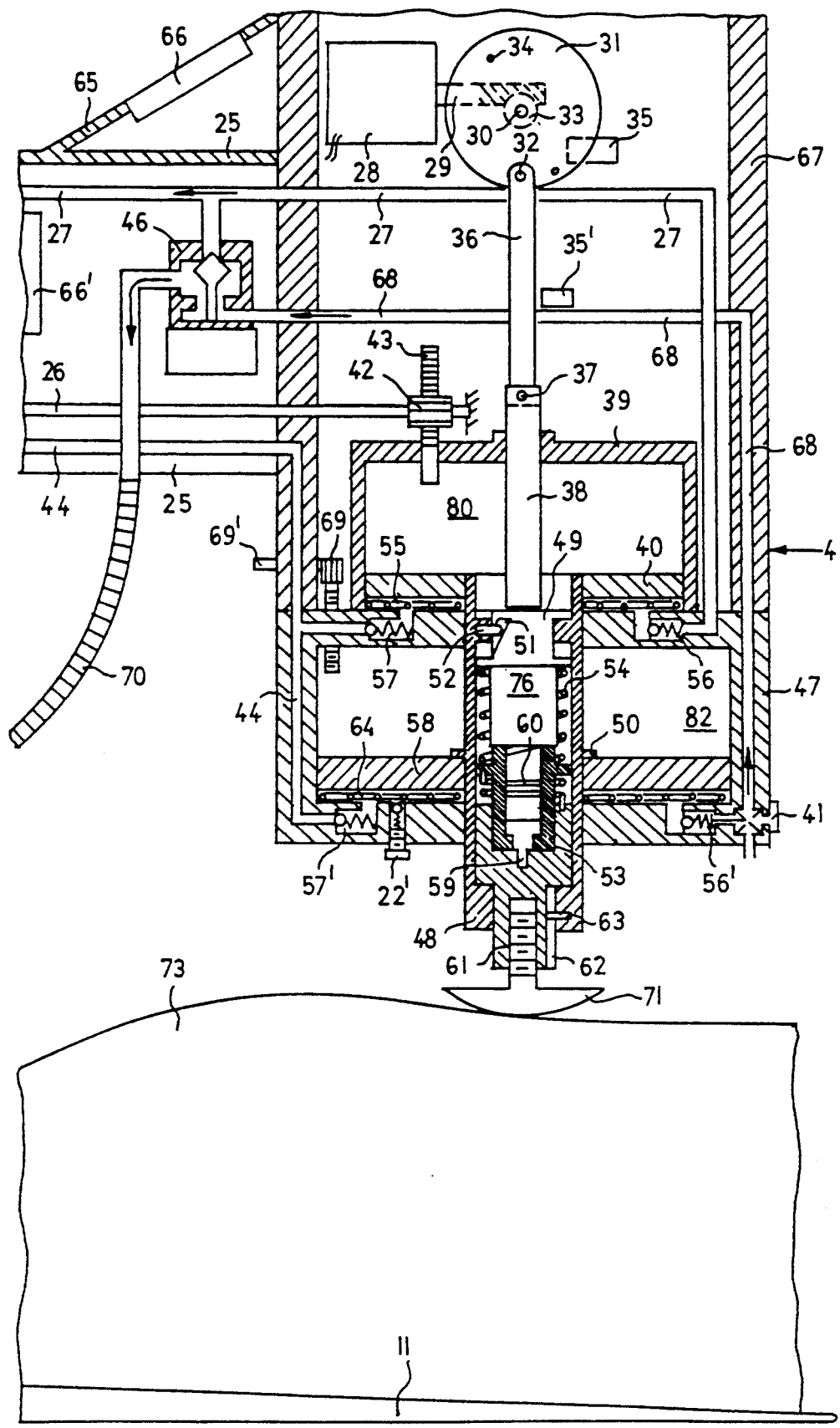
FIG. 5 is a cross-sectional view of the drive mechanism support of the embodiment shown in FIG. 1 showing details of the ventilation cylinders and thumping mechanisms at line I—I at the end of the compression cycle.
Figure 7:
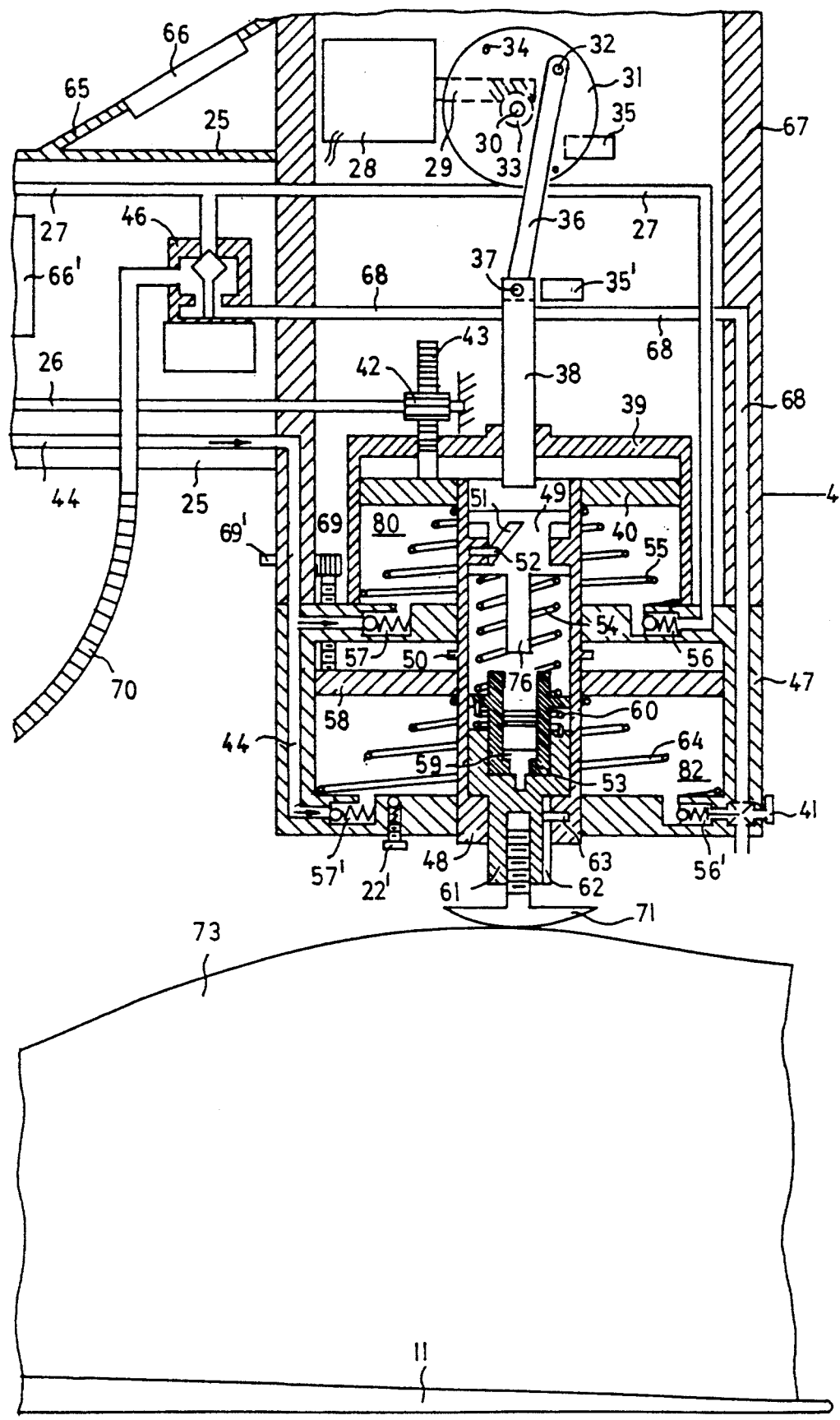
FIG. 7 is a cross-sectional view of the drive mechanism support of the embodiment shown in FIG. 1 showing details of the thumper, and thumper drive mechanisms during the upstroke of the decompression cycle at,line I—I.

A patient is positioned on top of the base 11 and beneath the thumper 71 such that the sternum of the patient's chest 73 is directly beneath the thumper 71 and just touching thumper 71 when thumper 71 is in its upper position as shown in FIG. 7. With reference to FIGS. 4 and 5, patient chest compression is achieved in the following manner. An electric motor 28 powered by any convenient means such as internal batteries 45, external AC power source or external 12 V D.C. power source (not shown), provides rotary motion along a motor shaft with worm wheel 29. The motor shaft with worm wheel 29 is engaged upon a crank shaft with worm gear 33, rotatably mounted on a drive mechanism wheel pivot 30 which is secured to housing 67. The crank shaft with worm gear 33 is fixed to one side of a drive mechanism crank wheel 31 similarly mounted on the drive mechanism wheel pivot 30. This gear arrangement provides speed reduction to the rotation speed of the motor 28. A crank arm shaft 36 is pivotally connected to the drive mechanism crank wheel 31. Rotation of the motor shaft thereby converts rotary motion to reciprocating linear motion.

The crank arm shaft 36 is connected to a plunger 38 by a plunger pivot 37. The plunger 38 passes through and is constrained by the top portion of a ventilation cylinder 39 to up and down vertical motion. The plunger 38, in its downward stroke, engages the thumper locking mechanism key 49 and pushes it downward. Thumper locking mechanism key 49 is provided with a thumper locking mechanism key guide pin 52 which cooperates with spiral slot 51.

Figure 10:
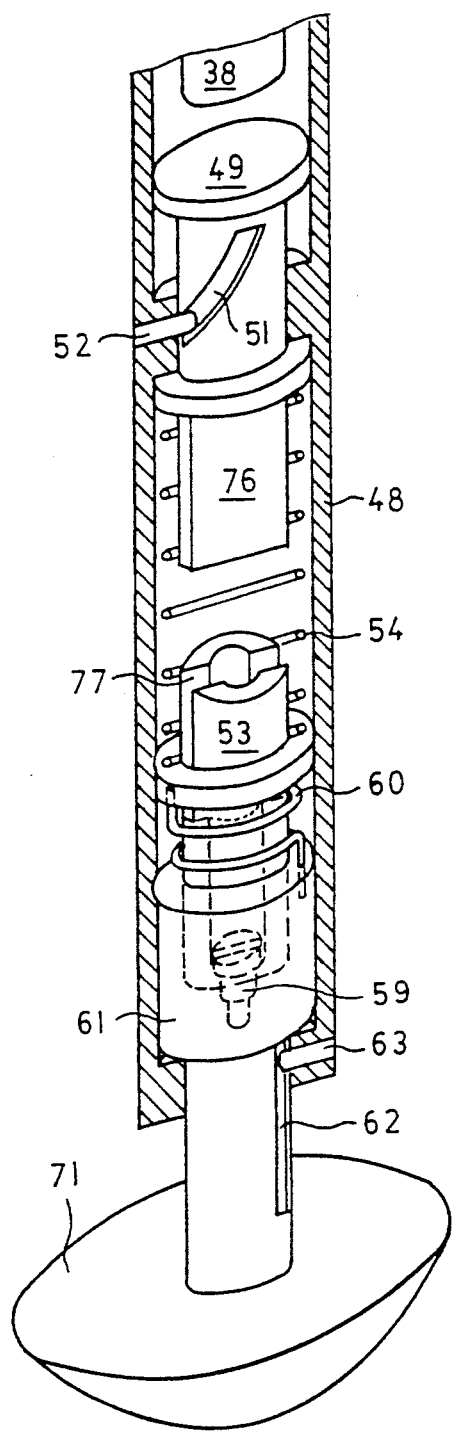
FIG. 10 is an enlarged isometric view of the locking mechanism shown in FIG. 7.

Locking key 49 which has a cylindrical upper section having a spiral groove or slot 51 in its outer circumference and a dependent rectangular flange 76 at the lower end thereof (FIG. 7), is mounted within thumper shaft 48. As key 49 moves up and down in shaft 48 by movement of plunger 38 it is caused to rotate by guide pin 52 which engages in spiral slot 51. As seen more clearly in FIG. 10, the lower portion 53 of the locking mechanism is also cylindrical in shape and is provided with a radial slot 77 into which flange 76 may slide, as described hereinafter. During the compression stroke in each cycle, key 49 moves downwardly and rotates so that flange 76 is misaligned with slot 77 and cannot enter it so that the downward movement is thus transmitted through lower portion 53, thumper yoke 61 to which lower portion 53 is secured by pivotal screw 59, and thence to the thumper 71 which is threadably connected to yoke 61 at the lower end thereof, thus compressing the patient's chest (FIG. 5). Key 49 compresses spring 54 on its down stroke and at the end of the compression stroke (FIG. 5), key 49 is urged upwardly by spiral decompression spring 54, separates from lower key 53 and rotates back to its initial position under the action of pin 52 in slot 51. The flange 76 is now in alignment with radial slot 77 but separated therefrom.

The thumper shaft 48 is part of the locking mechanism and travels longitudinally with key 49 and is connected to the ventilation cylinder piston 40 within the ventilation cylinder 39 whereby downward motion of the thumper shaft 48 causes an increase in pressure within the ventilation chamber 80 beneath the lower surface of the ventilation cylinder piston 40. An increase in ventilation chamber 80 pressure opens outlet check valve 56 thereby enabling expulsion of ventilation chamber 80 gases through said valve 56 to ventilation reservoir tube 27 and resilient reservoir 23.

The resilient reservoir 23 is provided with a resilient reservoir stretching rod 24 to prestretch the reservoir 23 so as to ensure complete emptying thereof.

The downward stroke of the ventilation cylinder piston 40 also compresses ventilation piston return spring 55 within ventilation chamber 80. Spring 55 returns ventilation cylinder piston 40 and thumper shaft 48 to the resting position during the upstroke of plunger 38. Negative pressure within ventilation chamber 80 opens inlet check valve 57 enabling entry of ventilation gases into the ventilation chamber 80 from an external source.

When the VDC mode is selected and the thumper shaft 48 moves downwards, the thumper shaft collar 50 engages the ventilation-during-compression (VDC) cylinder piston 58. An increase in pressure within the VDC chamber 82 opens VDC outlet check valve 56' thereby enabling expulsion of gases through VDC select valve 41, VDC outflow tube 68, three way solenoid valve 46, ventilation tube 70, ventilation valve 72', ventilation mask 72 and thence to the patient's lungs. The downward motion of VDC cylinder piston 58 compresses VDC piston return spring 64 within a VDC chamber 82. Preferably, springs 55 and 58 are conical spirals so that they flatten when compressed thus enabling improved volume control of the ventilation gases as there is minimum dead space under the pistons at the end of the down stroke. Said VDC piston return spring 64 returns VDC cylinder piston to its resting position during the upstroke of thumper shaft 48. During the piston 58 upstroke, negative pressure within VDC chamber 82 opens VDC inlet check valve 57' enabling entry of fresh ventilation gases into the VDC chamber 82 from an external source. The VDC inlet check valve 57 closes at the top of the upstroke.

At the completion of the downstroke of the ventilation cylinder piston 40 and the VDC cylinder piston 58, outlet check valve 56 and VDC outlet check valve 56' both close. The resulting stop in gas flow through the inlet side of ventilation valve 72' causes the outlet side of ventilation valve 72' to open, whereby gases within the patient's lungs are expelled by pressure within the lungs and the natural spring force of the chest to the atmosphere.

At the same time, the ventilation cylinder piston 40, thumper shaft 48 and thumper 71 move upwardly thereby decompressing the patient's chest 73, rising under its own spring action.

At the completion of a selected number of compression cycles, preferably five, the resilient reservoir 23 has been filled by the emptying of the ventilation chamber 80. The volume of gas in the reservoir 23 is proportional to the chest size of the patient. At this point, the three way solenoid valve 46 opens in response to the electronic control circuit (66) signals which stops the thumping stroke at top dead centre (34, 35) enabling gases within the resilient chamber 23 to be passed through ventilation reservoir tube 27, three way solenoid valve 46, ventilation tube 70, ventilation valve 72', ventilation mask 72 to the patient's lungs.

Figure 8:
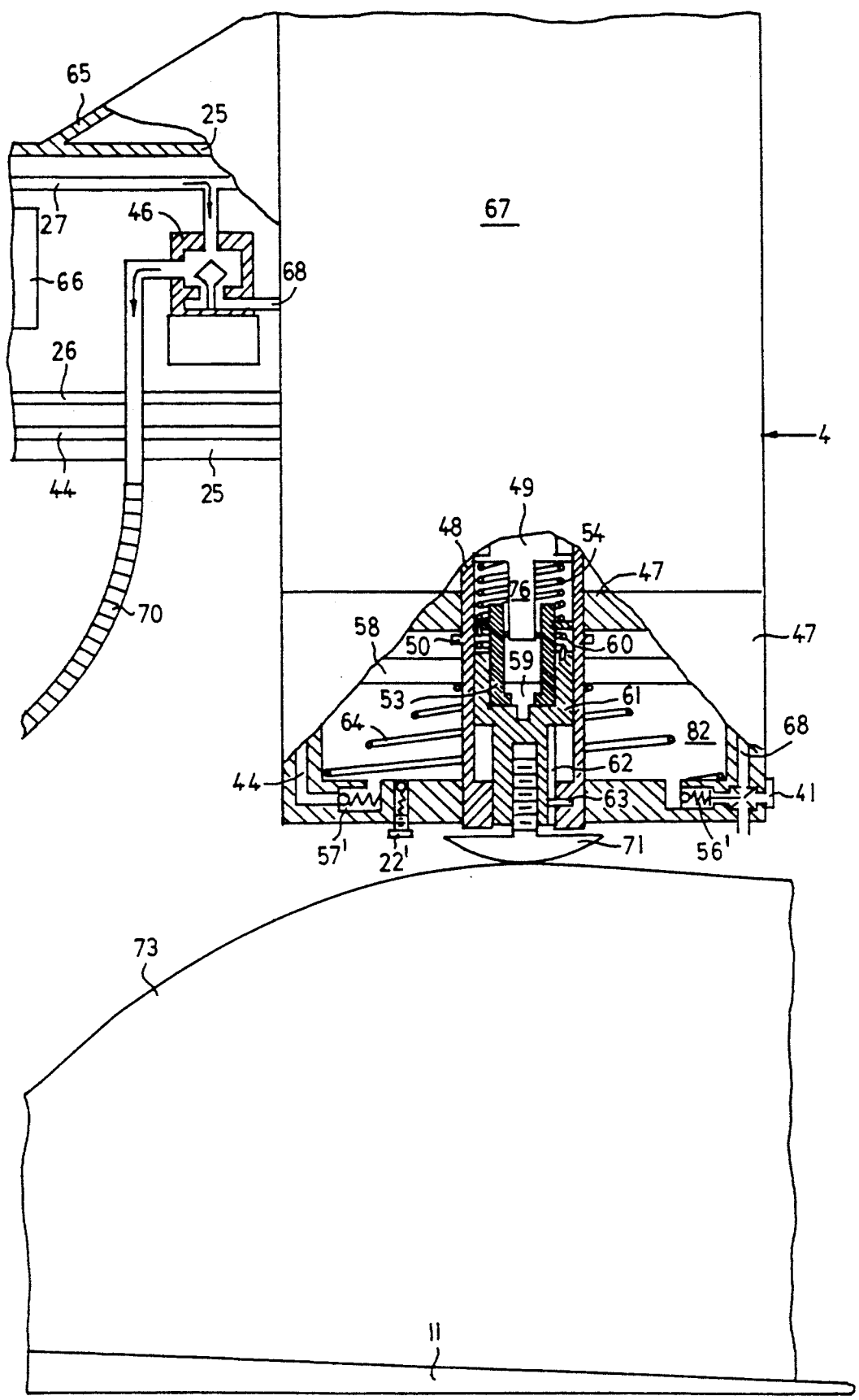
FIG. 8 is a cutaway cross-sectional view of the drive mechanism support of the embodiment shown in FIG. 1 showing details of the thumper, locking mechanism and thumper drive mechanisms during asynchronous ventilation at line I—I.

At this point in the cycle (FIGS. 8 and 10), the flange 76 on key 49 and slot 77 on lower portion 53 are aligned, so that when the thumper 71, yoke 61 and locking mechanism 53 rise in response to the patient's rising chest, lower portion 53 rises so that the slot 77 surrounds flange 76. The locking mechanism 53 compresses the thumper locking mechanism spring 54 during this action. After ventilation, patient's chest descends to rest position, spring 54 decompresses and returns thumper 71 through locking mechanism lower portion 53 and yoke 61 to its resting position.

In order to ensure that slot 77 and flange 76 always remain in their respective orientations a spiral tension spring 60 is secured between lower portion 53 and thumper yoke 61 which is tightened as flange 76 turns lower portion 53 when it descends in mating engagement with slot 77. As soon as flange 76 disengages from slot 77, spring 60 unwinds and returns slot 77 to its rest position. Spring 60 is, in effect, a safety device to spring load key 53 in case of improper setting of the height adjustment.

As inhalation is completed, the pressure drops within the resilient reservoir 23 and ventilation valve 72', thereby opening the exhalation port within the ventilation valve 72'. Exhalation results from the gas pressure within the patient's lungs and the natural spring force of the patient's chest 73. The thumper 71, thumper yoke 61 and locking mechanism 53 return to their initial position by decompression of the thumper locking mechanism spring 54. This action completes one full CPR cycle.

Another feature of the device enables the operator to select a "ventilation without compression" (VWC) mode. When the arm 25 with attached to it drive mechanism housing 67 is removed from above patient chest and the VDC select valve 41 set to VWC position, opens check valve 56' and bypasses the ventilation mask 72 during compression whereby gases from the VDC chamber 82 are expelled to the atmosphere. Similarly, the VDC select valve can be partially opened to permit closure of the exhalation port in valve 72' which therefore prevents exhalation from the lungs during compression which causes increased intra-thorax pressure.

The device can be easily configured to patients with different chest sizes by adjustment of the distance between the thumper 71 and base 11 to accommodate the patient's chest 73. A span adjustment crank 20 is provided on the upper surface of the arm 25 (FIG. 4). The span adjustment crank 20 is connected to a span adjustment screw 16 which cooperates with a span adjustment nut 17. The span adjustment nut 17 is mounted on the upper surface of a span adjustment nut extension tube 18 extending vertically from a bracket 18' which is fixed to the lower region of the internal telescoping column as shown in FIG. 4. Actuation of the span adjustment crank 20 causes the span adjustment screw 16 to move relative to the span adjustment nut 17, thereby causing the external upright telescope column 12 to move relative to internal upright telescope column 13. This changes the distance between the base 11 and thumper 71, thereby enabling adjustment for different patient's chest sizes. Movement of adjustment crank 20 is sensed by span adjustment sensor 75 which automatically feeds this information to CPU 90. Based on the information from sensor 75, the CPU 90 adjusts thumper compression force by controlling the motor current in speed controller 95.

The shaft of the span adjustment screw 16 also has a stroke adjustment worm gear 19 engaging a stroke adjustment gear 19' mounted on a stroke adjustment shaft 26 within the arm 25. The stroke adjustment shaft 26 is rotatably mounted between the vertical upright 3 and the drive mechanism support 4 and extends inside and along the arm 25. The thumper-side stroke adjustment gear 42 is mounted on the stroke adjustment shaft 26 and engages with the thumper-side stroke adjustment rack 43. The thumper-side stroke adjustment rack 43 cooperates with the ventilation cylinder piston 40 through the ventilation cylinder 39. Movement of the thumper-side stroke adjustment rack 43 downwardly, limits the upward displacement of the ventilation cylinder piston 40, and the attached thumper shaft 48, VDC cylinder piston 58, thumper yoke 61 and thumper 71 relative to the plunger 38 by delaying engagement of plunger 38 with the thumper locking mechanism key 49.

Actuation of the span adjustment crank 20 thereby enables the device 2 to be adjusted for different chest sizes (span adjustment) simultaneously and proportionally with the length of stroke, the ventilation volume within ventilation chamber 80 and the VDC volume within VDC chamber 82. For a larger patient, a greater stroke length and higher ventilation volume is required. Therefore, adjustment of the span adjustment crank 20 to increase the distance between the base 11 and thumper 71, simultaneously and proportionally increases the thumper length of stroke and the ventilation volumes.

The maximum ventilation pressure in resilient reservoir 23 can be adjusted through the adjustable pressure relief valve 22. The pressure relief valve 22 releases pressure in excess of a preselected level.

Additional adjustment to the VDC volume can be made by actuation of the VDC volume adjustment arm 69' which engages the VDC volume adjustment screw 69. The VDC volume adjustment arm 69' engages the upper surface the VDC cylinder piston 58 inhibiting its upward motion as shown in FIG. 7. This adjustment additionally reduces the ventilation during compression volume relative to the length of chest compression stroke.

The maximum ventilation pressure during compression is adjusted by the VDC pressure relief valve 22'. This valve 22' is provided to ensure a maximum ventilation during compression is not exceeded.

The CPR device 2 is provided with a crank shaft top dead centre indicator 34, and a crank shaft top dead centre sensor 35 to ensure the crank shaft arm 36 returns to the dead centre position after each chest compression, so that the patient's chest 73 is not compressed.

Figure 6:
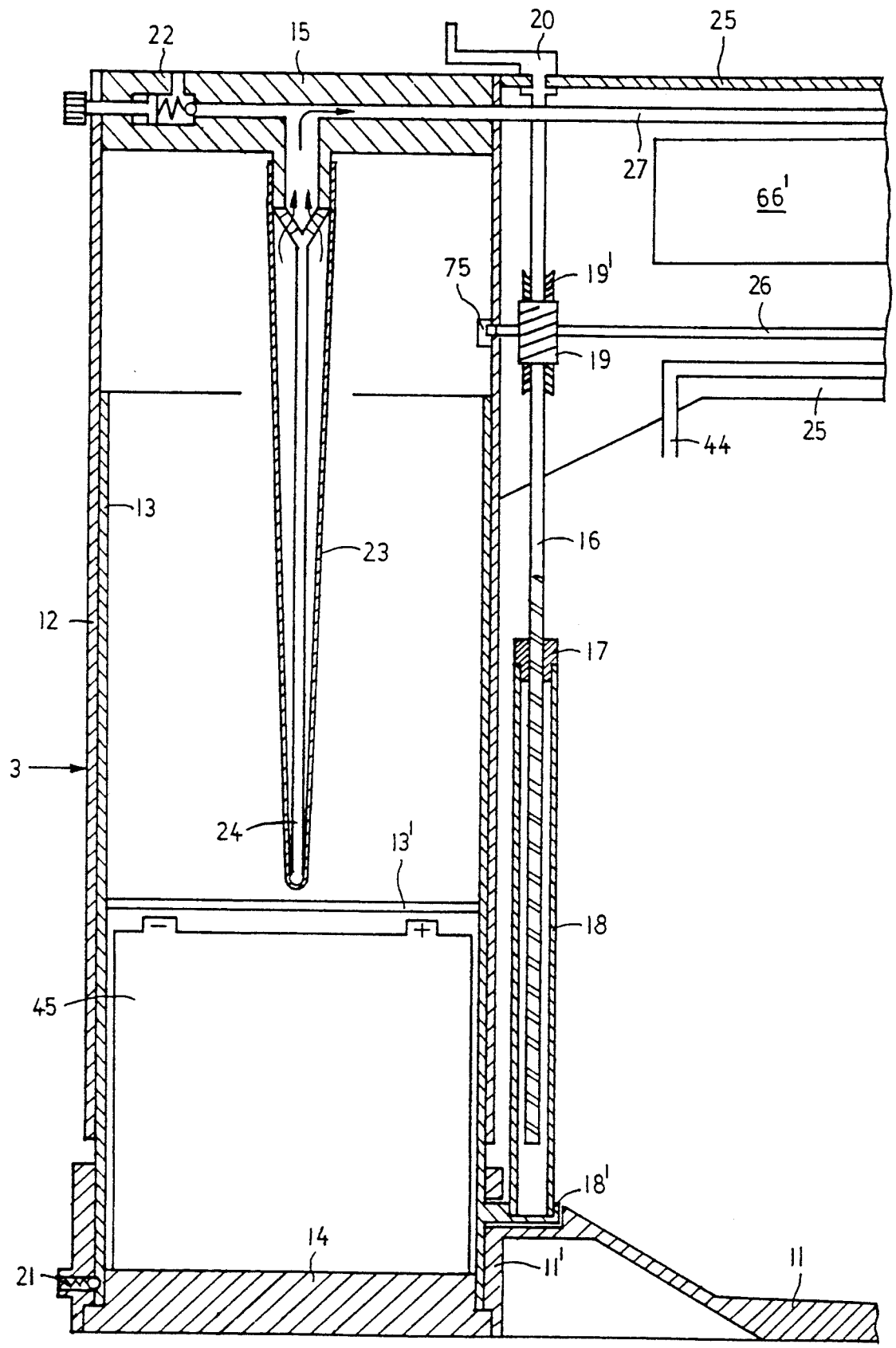
FIG. 6 is a cross-sectional view of the upright support of the embodiment shown in FIG. 1 showing details of the resilient reservoir during emptying and span adjustment crank at line I—I.

The CPR device 2 can be removed from the patient's chest in order to perform ventilation only in the event that chest compression is not required or to administer electric shock by applying sufficient lateral force to the arm 25 in order that the spring loaded arm locking mechanism 21 (FIG. 6) disengages to allow rotation of column 3 and attached the arm 25 relative to the base 11 (FIGS. 2 and 3).

Figure 9:
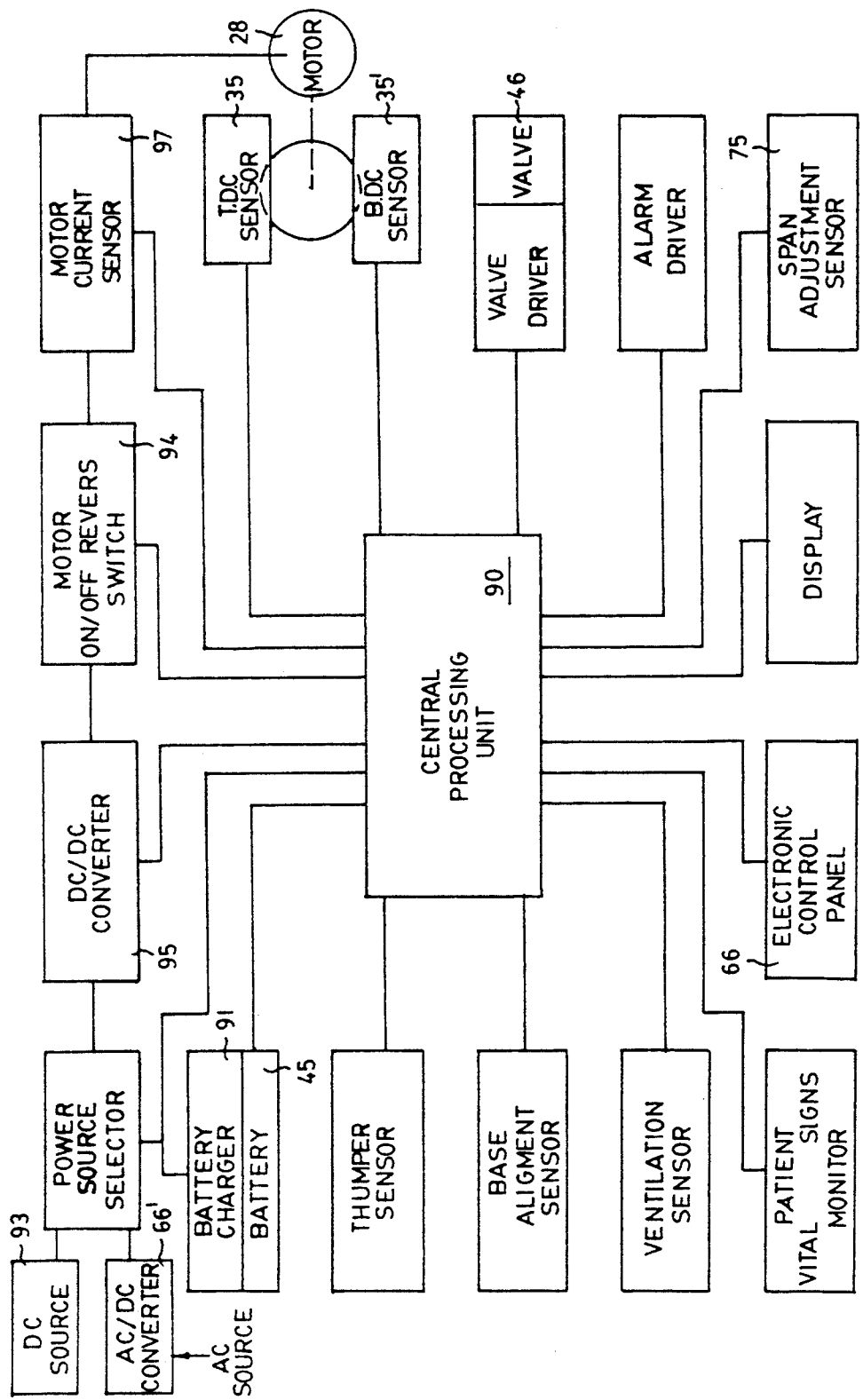
FIG. 9 is a block diagram illustrating the electrical circuits associated with the embodiment of FIG. 1.

Electronic control of the motor 28 and solenoid valve 46 is achieved by circuitry in electronics panel 66 which is located within electronic panel housing 65. FIG. 9 illustrates in schematic form the circuitry which may be contained in electronics panel 66. Power may be provided to the device by internal battery 45, which may be charged by battery charger 91 connected to a power source; or by an external AC source 92 or by an external DC source 93. If an AC source is used an internal AC/DC converter 66' is provided. Motor 28 is controlled, via a central processing unit (CPU) 90, through an on/off switch 94, speed controller 95, reversing switch 96 and current sensor 97. Solenoid valve 46 is also controlled by CPU 90 via a valve driver 98. The motor reversal switch 96 is used to reverse rotation of the motor 28 to interrupt thumper 71 compression and withdraw it to top-dead-centre whenever thumping force exceeds a preset value.

It will be appreciated that CPU 90 includes a counter which counts the number of compression strokes and when it reaches the preset number preferably but not essentially five, the motor 28 pauses, valve 46 opens allowing gases stored in reservoir 23 to pass to patient 73, via mask 72. The duration of the pause in motor 28 is controlled by a timer in CPU 90, and after the pause valve 46 closes and the cycle is repeated.

A preferred embodiment has been set forth in the description and drawings and is intended for illustration and not limitation. Various changes can be made without departing from the spirit and scope of the invention.

The embodiment of the invention in which an exclusive right or property is claimed are defined as follows:

1. An apparatus for administrating cardiopulmonary resuscitation comprising:
    a base member for supporting a patient's back;
    a chest compression means for administrating chest compression to a patient, said chest compression means having a thumper means and mounting means on said base member means such that a patient's sternum be positioned between said thumper means and said base member means;
    drive means for reciprocatingly translating said thumper means toward and away from said base member means for cyclically compressing and releasing the chest of a patient;
    ventilation means for providing respirable gas, operatively coupled to said plunger means;
    adjustment means controlling the adjustment of chest compression means and ventilation means;
    control means for controlling the operation of the drive means, ventilation means and monitoring a patient's vital signs.

2. The apparatus of claim 1 wherein said mounting means includes span adjustment means for accommodating different chest sizes.

3. The apparatus of claim 1 wherein said mounting means includes a swing arm coupled to a telescope upright which is rotatably mounted to said base member means.

4. The apparatus of claim 1 wherein said adjustment means includes means for adjusting the volume of respirable gas delivered by said ventilation means and for adjusting said length of stroke and relative force of compression applied by said chest compression means in proportion to a patient chest size wherein said adjustment means is operatively coupled to the mounting means for accommodating different chest sizes.

5. The apparatus of claim 1 wherein said ventilation means further comprises a low pressure ventilation means for supplying respirable gas to a patient notwithstanding the position of the adjustable mounting means.

6. The apparatus of claim 1 wherein said ventilation means further comprises a high pressure ventilation means for supplying respirable gas to a patient only during chest compression by said thumper means where.

7. The apparatus of claim 1 wherein said mounting means comprises a ratchet means operatively coupled to said thumper means for holding thumper means in a reset position and allowing compression by said drive means and further allowing expansion of the chest during patient inhalation.

8. The apparatus of claim 1 further comprising control means for selectively operating the chest compression means and the ventilation means in a predetermined sequence.

9. The apparatus of claim 8 wherein said ventilation means further comprises:
    low pressure ventilation means for supplying respirable gas to a patient after preselected number of chest compression;
    low pressure ventilation means for supplying respirable gas to a patient notwithstanding the position of the adjustable mounting means; and
    high pressure ventilation means for supplying respirable gas to a patient only during chest compression by said thumper means.

10. The apparatus of claim 1 wherein said ventilation means further comprises a low pressure ventilation means for supplying respirable gas to a patient after preselected number of chest compressions.

* * * * *